(12) United States Patent
Garbez et al.

(10) Patent No.: US 10,994,875 B2
(45) Date of Patent: May 4, 2021

(54) DEVICE AND METHOD FOR TRANSFERRING BREAST MILK FROM AN IRREGULAR SHAPED RESERVOIR ASSEMBLY FOR STORAGE OR FEEDING

(71) Applicant: DAO Health, El Dorado Hills, CA (US)

(72) Inventors: Dan Garbez, El Dorado Hill, CA (US); Stella Dao, El Dorado Hills, CA (US); Ben Sutton, Scotts Valley, CA (US); Dave Paul, Scotts Valley, CA (US); Ron Briggs, Granite Bay, CA (US)

(73) Assignee: DAO Health, El Dorado Hills, CA (US)

( * ) Notice: Subject to any disclaimer, the term of this patent is extended or adjusted under 35 U.S.C. 154(b) by 147 days.

(21) Appl. No.: 15/785,650

(22) Filed: Oct. 17, 2017

(65) Prior Publication Data
US 2018/0105302 A1 Apr. 19, 2018

Related U.S. Application Data

(60) Provisional application No. 62/410,099, filed on Oct. 19, 2016.

(51) Int. Cl.
| | |
|---|---|
| *B65B 39/00* | (2006.01) |
| *A61J 9/00* | (2006.01) |
| *A61M 1/06* | (2006.01) |
| *A61J 11/04* | (2006.01) |

(52) U.S. Cl.
CPC .............. *B65B 39/007* (2013.01); *A61J 9/00* (2013.01); *A61J 11/04* (2013.01); *A61J 11/045* (2013.01); *A61M 1/062* (2014.02)

(58) Field of Classification Search
CPC ...... B67D 3/0029; B67D 3/0035; B67C 9/00; B67C 11/02; B65B 39/06; B65B 3/06
USPC ..................... 141/391, 363–366, 375, 86–88
See application file for complete search history.

(56) References Cited

U.S. PATENT DOCUMENTS

| | | | | |
|---|---|---|---|---|
| 2,767,744 A | * | 10/1956 | Beerman ................... | B65B 3/04 141/319 |
| 3,230,986 A | * | 1/1966 | Worley .................... | A47L 19/04 141/375 |
| 5,297,600 A | * | 3/1994 | Downes .................... | B67C 9/00 141/106 |
| 6,585,016 B1 | * | 7/2003 | Falligant ............. | A61M 16/183 141/352 |
| 8,118,066 B2 | * | 2/2012 | Muhlhausen .......... | B65D 47/06 141/18 |
| 8,702,646 B2 | | 4/2014 | Garbez et al. | |
| 2003/0106612 A1 | * | 6/2003 | Vincent, III ....... | B65D 81/3211 141/383 |

(Continued)

*Primary Examiner* — Timothy P. Kelly
(74) *Attorney, Agent, or Firm* — Rockman Videbeck & O'Connor

(57) ABSTRACT

A liquid milk transfer system for conveying milk from a milk reservoir device to a milk storage container. A support structure has a first opening that communicates with an interior of the milk storage container. The first opening of the support structure has an irregular circumferential shape partially the same as partial surface dimensions of the milk reservoir. The first opening receives and supports the milk storage container with a pouring spout positioned below the first opening, and the pouring spout located above the interior of the milk storage.

5 Claims, 3 Drawing Sheets

(56) References Cited

U.S. PATENT DOCUMENTS

2014/0378946 A1 12/2014 Thompson et al.
2015/0217035 A1 8/2015 Pollen et al.

* cited by examiner

DEVICE AND METHOD FOR TRANSFERRING BREAST MILK FROM AN IRREGULAR SHAPED RESERVOIR ASSEMBLY FOR STORAGE OR FEEDING

CROSS-REFERENCE TO RELATED APPLICATION(S)

This application claims priority to U.S. Provisional Application No. 62/410,099, filed Oct. 19, 2016, to the extent allowed by law and the contents of which are incorporated herein by reference in their entireties.

TECHNICAL FIELD

This invention relates to the field of human breast milk collection and storage devices and more specifically, a breast milk transfer system for transferring breast milk from a milk collection device initially lodged in a lactating woman's brassiere to a specially configured milk storage or feeding receiving container that readily receives and supports the collection device while milk is transferred to the storage or feeding receiving container.

BACKGROUND

Breast pumps are well known, but the field of breast pump devices with self-contained breast milk reservoirs which can be used discreetly by fitting them within a woman's brassiere, often under ordinary clothing so that a woman can use a breast pump around others discreetly, is relatively new. The only known devices in this field, upon which this invention improves, are taught in U.S. Pat. Nos. 7,559,915; 8,118,772 and 8,702,646 (Dao, Garbez), the disclosures of which patents are incorporated by reference herein.

The above-mentioned patents disclose a milk collecting reservoir generally cup-shaped to fit into a lactating woman's brassiere, which reservoir is adapted to be disconnected from a pump and emptied when full after hands-free operation, whereby the milk can be transferred to a feeding or milk storage container such as a baby bottle or pliable storage bag. If the milk is to be used to feed a baby upon emptying the reservoir, the milk is poured into a baby bottle, and then a nippled cap is fastened to the opening of the baby bottle. The nipple is then placed in the baby's mouth. If the milk removed from the reservoir is to be stored, the baby bottle, or other container to which the milk is transferred from the reservoir, is capped or sealed and stored in a refrigerated environment. If desired, the breast milk in the reservoir can be transferred to a pliable bag.

The naturally shaped breast milk collection systems disclosed in the patents identified above include a pour spout which creates a narrow stream when the reservoir assembly is removed from the brassiere and inverted, allowing the milk to be poured into a baby bottle or other container without the use of any additional devices, funnels or gear. But a need exits for a milk transfer device to aid in this process, to reduce the risk of spillage for some users who are fatigued, or are unsteady, or may simply desire to use these collection systems in conjunction with narrow-mouthed baby bottles or storage bags, but who worry about the increased risk of spillage when trying to pour the milk into a bottle with a small opening. Additionally, more and varying shapes and sizes of breast milk collection systems are being developed with irregular shapes that may be difficult to maintain steady during pouring. There is an additional need for users of these milk collection devices to have greater choices in the selection of baby feeding and milk storage bottles they use in combination with these breast milk collection systems.

SUMMARY

A liquid milk transfer system for conveying milk from a milk reservoir device to a milk storage container is disclosed. The subject system is particularly useful for transferring breast milk from a generally cup-shaped reservoir that fits into a lactating woman's brassiere during milk expression. The disclosed device includes a support structure having a first opening that communicates with the interior of the milk storage container. The first opening of the support structure has an irregular circumferential shape that is partially the same as partial surface dimension of the milk reservoir device, such as the first opening having a linear position and a curved portion. The milk reservoir device has a pouring spout, and the irregular circumferential shape of the first opening receives and supports a linear and a curved surface of the milk reservoir device with pouring spout located above the interior of the milk storage container. Milk is transferred from the reservoir device to the storage container under the influence of gravity.

In one embodiment of the presently disclosed device, a baby bottle comprises a container with an irregularly shaped opening communicating with the interior of the bottle, and a nippled cap that sealingly mates with the neck of the container over the opening. Rather than have a regular circular opening at the upper opening of the container, the container opening of the embodiment of the presently disclosed device has two opposing approximately parabolic or irregular wave-shaped grooves or indentations, carved into the vertical upper ring-like structure comprising the opening of the container. These grooves are adapted to receive and support an assembled, inverted, milk reservoir after the reservoir has been filled, or partially filled, with breast milk and removed from the lactating woman's brassiere. The milk will drip from a pouring spout in the inverted reservoir and into the container.

In this embodiment of the invention, a cap assembly can be attached to the neck surrounding the opening of the container, using a snap fit, screw threads, or other fastening assemblies as are known in the art. The cap assembly includes, in an embodiment, a nipple at the top, and a downwardly extending circular portion that covers and seals the parabolic or wave shaped grooves in the neck surrounding the opening of the container so that milk cannot escape from the grooves after the cap assembly has been attached to the neck of the container.

In a further embodiment, a separate support structure comprises a hollow cylindrical, or tubular shape adapted to fit over a baby feeding bottle to be filled with breast milk from a reservoir. The support structure has two opposed approximately parabolic or irregularly shaped grooves or indentations carved into the circular upper ring-like circumference of the opening leading to the interior of the support structure. The opposed grooves are adapted to receive and support an assembled, irregularly shaped milk reservoir after the reservoir has been filled or partially filled with breast milk and removed from the lactating woman's brassiere. An optional axially disposed funnel structure may be molded or otherwise formed or located in the interior of the support structure to guide the milk dripping from the reservoir into the bottle located beneath the support structure, with the lower aperture of the funnel positioned above or into the upper plane of the opening of the container, which container is disposed immediately below the opening of the support structure. This second embodiment is configured to allow an irregularly shaped reservoir to be supported in a pouring position above a standard baby bottle that has a fully circular opening, without parabolic or irregular wave shaped grooves formed in the neck surrounding the opening of the bottle.

Another embodiment of the presently disclosed milk transfer system comprises a stand and optional funnel combination structure adapted to securely support and hold an irregularly shaped breast milk reservoir in a pouring position over a baby bottle to be filled. The funnel guides the breast milk into the baby bottle, whose opening is located below the lower end of the funnel structure. The upper portion of the stand has an irregular shaped opening that supports the irregularly shaped reservoir in its inverted pouring position when the reservoir is placed in and supported by the opening. This embodiment also optionally includes at least one hook adapted to support a pliable storage container beneath the reservoir.

A further embodiment of the presently disclosed pouring system comprises a uniquely configured baby feeding bottle that has a mono-planar irregularly shaped opening, the opening having linear and curved surfaces shaped to engage and support the irregular surfaces of the breast milk containing reservoir when the inverted reservoir is placed in the opening. A flared portion of the bottle beneath the irregularly shaped opening terminates in a round configuration at the point where the flared portion meets the circular portion of the bottle. If the bottle is other than circular in the horizontal plane, the lower end of the flared portion takes the shape of the horizontal configuration of the bottle.

DETAILED DESCRIPTION

The presently disclosed milk transfer system will be more fully understood by reference to the following drawings of the illustrated embodiments, which drawings are for illustrative purposes only and are not to be considered as limiting the scope of the claims.

Figure 1:
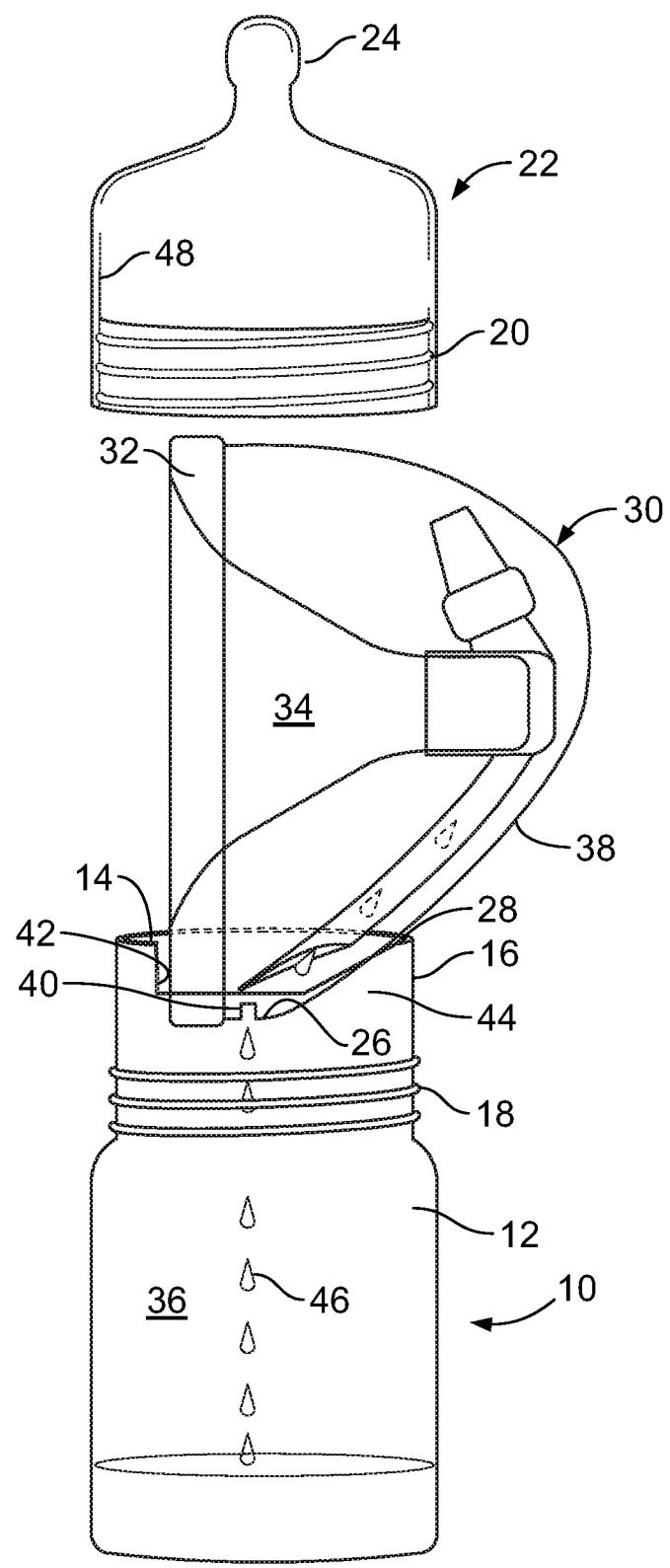
FIG. 1 is an exploded perspective view of an embodiment of a baby feeding bottle having an upper opening with opposed irregular shaped grooves, a breast milk containing reservoir supported in an inverted position by the irregularly shaped grooves, and a cap assembly that is secured to the baby feeding bottle when the reservoir is removed from the irregularly shaped grooves upon the transfer of the breast milk from the reservoir to the bottle.

FIG. 1 illustrates one embodiment of the presently disclosed system having a milk storage container 10 such as a baby feeding bottle comprising an interior container portion 12 and an irregular shaped opening 14 formed at the top of a neck portion 16 of container 10, such that opening 14 communicates with the interior portion 12 of container 10. The neck 16 in the illustrated embodiment includes a threaded portion 18 to engage mating threads 20 of cap 22, as will be explained. Cap 22 includes a pliable nipple 24 for insertion into a baby's mouth when container 10 contains milk.

The opening 14, rather than having a regular mono-planar circular shape as is common with most container openings, comprises two opposed approximately parabolic or irregular wave-shaped grooves or indentations 26, which grooves 26 extend vertically downward from the upper lip 28 forming the opening 14. The grooves 26 are adapted to receive and support an assembled breast milk reservoir 30, after the filled or partially filled reservoir is removed from the lactating woman's brassiere. The reservoir 30 is more completely described and illustrated in commonly assigned U.S. Pat. Nos. 7,559,915; 8,118,772; and 8,702,646, which disclosures are incorporated herein by reference.

As seen in FIG. 1, the reservoir 30 has a circumferential ring 32 extending around a funnel-shaped interior 34 that guides breast milk into the hollow interior 36 when the reservoir is used to store breast milk expressed by a woman while wearing reservoir 30 under her brassiere. Reservoir 30 also has a somewhat cup-shaped surface 38 forming an outer edge of the reservoir. The reservoir 30 also includes a spout 40 from which breast milk can exit the reservoir when the reservoir is in the inverted position shown in FIG. 1.

The grooves 26 in neck portion 16 of container 10 each comprise a vertically extending surface 42 and a somewhat curved surface 44. As seen in FIG. 1, when reservoir 30 is partially inserted into grooves 26, each vertical extending surface 42 engages and supports a portion of circumferential ring 32, while somewhat curved surface 44 engages and supports a curved portion of cup-shaped surface 38 of the reservoir. The reservoir 30 is in an inverted position with spout 40 in a downward-facing position. With reservoir 30 inserted in grooves 26 of neck 16, the reservoir 30 is adequately supported over opening 14 of bottle 10, and milk pours through spout 26 and into the interior portion 12 of bottle 10, as indicated at 46, to transfer the milk to the bottle 10.

Referring to FIG. 1, following the successful transfer of breast milk from reservoir 30 into container 10, reservoir 30 is lifted up and removed from grooves 26 and then cleaned prior to further use. Cap 22 is then placed over opening 14 of container 10, and the cap is rotated with threads 20 engaging threads 18 until cap 22 seals opening 14 of the bottle. Cap 22 includes a downwardly extending portion 48 that completely covers and seals each groove 26 so that milk in container 10 cannot leak out of grooves 26. In most instances, container 10 with the breast milk inside will either be refrigerated, or used upon placement of cap 22 over opening 14 to feed a baby.

Figures 2A, 2B:
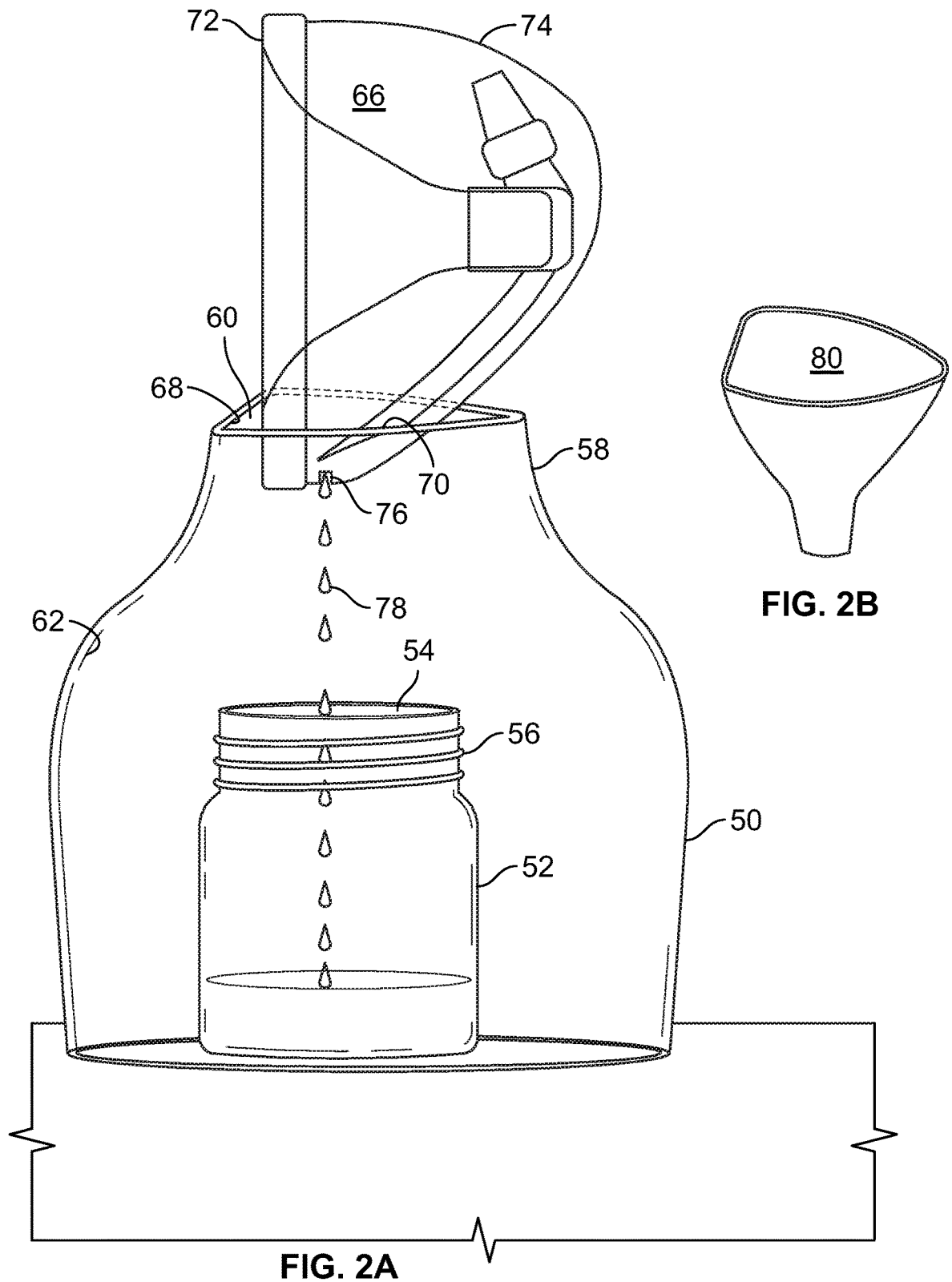
FIG. 2A is a perspective view of a second embodiment of the present invention comprising a support for a breast milk containing reservoir extending over a baby feeding bottle, the support having an irregularly shaped opening that supports the reservoir as breast milk is being transferred from the reservoir to the baby feeding bottle.
FIG. 2B is an optional funnel that forms part of the support of FIG. 2A, which funnel directs breast milk to the opening in the baby bottle upon the transfer of breast milk from the reservoir to the bottle.

FIGS. 2A and 2B illustrate a further embodiment of the present invention. In this embodiment, a circumferential hollow support 50 envelops and extends over a standard baby feeding container 52. Both the support 50 and the container 52 are standing on the same flat surface. Container 52 has a circular opening 54 and a threaded neck 56. A cap (not shown) similar to cap 22 shown in FIG. 1 can be threaded onto threads 56 as is known in the art.

Support 50, as illustrated, is somewhat bell shaped having an upper inwardly flared neck 58 and an opening 60. Opening 60 communicates with the interior 62 which is spacious enough to extend over baby feeding containers 52 of several sizes and shapes.

Opening 60 has two faces adapted to receive and support inverted reservoir 66, which is structured the same as reservoir 30 of FIG. 1. Opening 60 has a substantially vertical face 68 and a somewhat curvilinear face 70. When reservoir 66 is partially inserted into opening 60 as seen in FIG. 2A, vertical face 68 engages a portion of circumferential ring 72 of reservoir 66, and curvilinear face 70 engages a portion of the curved outer surface 74 of reservoir 66, thus holding reservoir 66 in a secure position such that the pouring spout 76 of reservoir 66 allows breast milk to be transferred into container 52, as shown at 78.

FIG. 2B illustrates an optional funnel structure 80 that can be formed inside of support 50 below opening 60 to direct the flow of breast milk 78 into bottle 52. Funnel 80 may also be detachable from support 50.

Figure 3A:
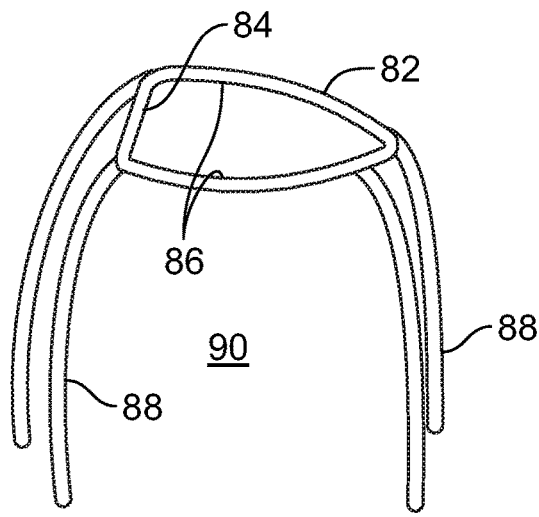
FIG. 3A is an alternate embodiment of the support of FIG. 2A comprising an irregular shaped support element for supporting a breast milk containing reservoir, with a plurality of legs positioning the support element over a baby feeding bottle in the manner shown in FIG. 2A.

FIG. 3A illustrates a further embodiment of the present invention, comprising an irregularly shaped reservoir support ring 82 adapted to receive and support a breast milk reservoir (not shown) similar to reservoirs 30 and 66 of FIGS. 1 and 2A. Irregularly shaped ring 82 has a flat portion 84 adapted to contact and support portions of the circumferential ring 72 (FIG. 2A) of the breast milk containing reservoir 66 (FIG. 2A) when the reservoir is inserted into ring 82. Ring 82 also comprises curvilinear portions 86 that are adapted to contact and support the outer surface 74 (FIG. 2A) of reservoir 66 (FIG. 2A) when the reservoir is inserted into ring 82. In this manner, reservoir 66 is supported in an inverted position directly below ring 82. Ring 82 is supported by several legs 88, creating a space 90 where a baby feeding container can be placed for filling when the inverted reservoir is placed in ring 82.

Figure 3B:
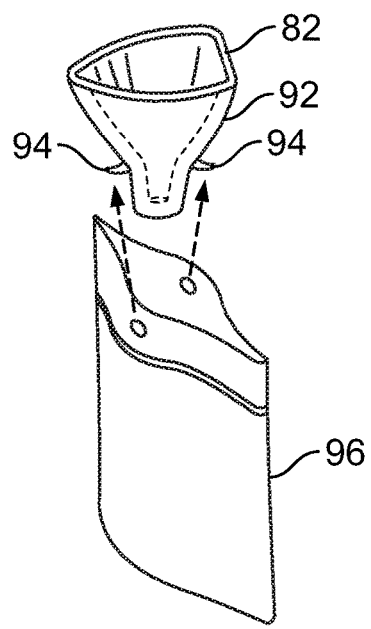
FIG. 3B is an optional funnel that can be attached to the support element of FIG. 3A, the funnel element including hooks adapted to removably attach storage bags to receive the breast milk transferred from the breast milk containing reservoir.

FIG. 3B illustrates an optional funnel 92 extending downward from ring 82 to assist in directing breast milk into a container located beneath ring 82 when milk is being transferred from the inverted reservoir, as explained previously. Hooks 94 extend outward from opposed sides of funnel 92 upon which a pliable storage bag 96 can be hung if the lactating woman desires to collect her breast milk in a pliable storage bag rather than a rigid container.

Figure 4:
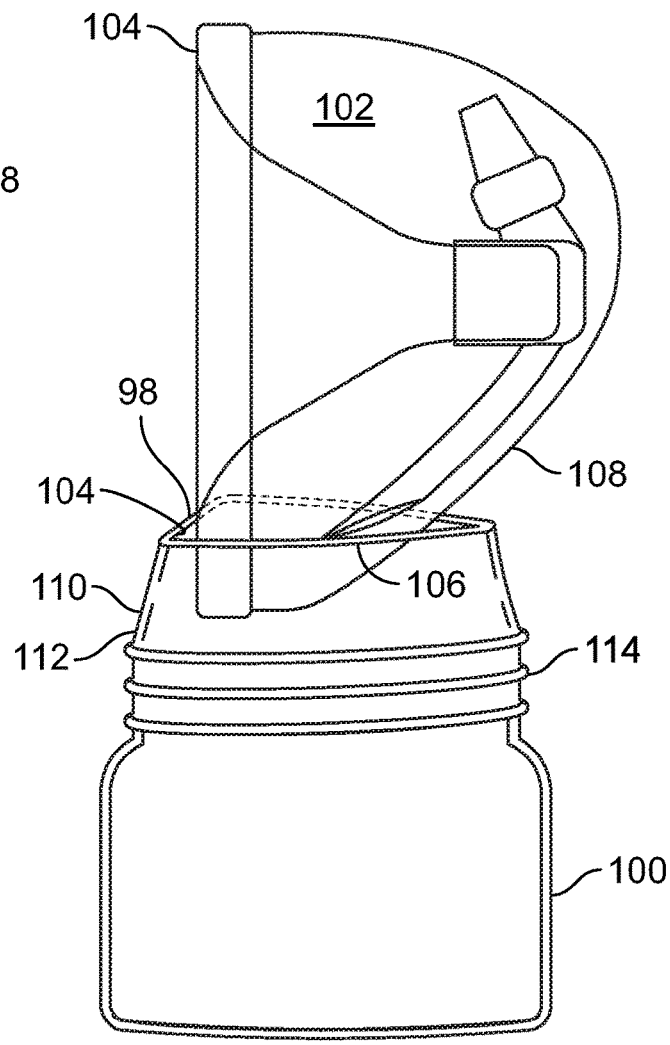
FIG. 4 is a further embodiment of a baby feeding bottle having a mono-planar opening, the opening having an irregular shape to engage and support the irregular shape of a breast milk containing reservoir.

FIG. 4 illustrates another embodiment of the presently disclosed device. In this embodiment, the irregularly shaped grooves in the opening of the bottle 10 of FIG. 1 are replaced by an irregularly shaped mono-planar opening surface 98 of bottle 100 that receives and supports the inverted reservoir 102. Opening surface 98 extends horizontally in a single plane. Portion 104 of surface 98 is substantially linear to contact and engage circumferential ring 104 of inverted reservoir 102. Portion 106 of surface 98 is curvilinear so as to contact and engage the curved outer surface 108 of inverted reservoir 102.

A flared neck portion 110 of container 100 extends downward to the circular portion 112 of container 100. Threads 114 are adapted to engage and secure a nippled cap 22 (FIG. 1) as previously described. If the bottle 100 has a cross-sectional configuration that is other than circular, the bottom of flared portion 110 conforms to the cross-sectional shape of the bottle.

The foregoing description of illustrated embodiment of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims set forth below.

What is claimed:

1. A liquid milk transfer system for conveying milk from a milk reservoir device having a pouring spout and partial surface contours, comprising:
   a. a milk storage device having an interior volume defined by at least one side wall and a bottom surface of the milk storage device;
   b. the milk storage device having a first opening, the first opening communicating with the interior volume of the milk storage device;
   c. the first opening of the milk storage device defined by at least one irregular shaped groove in an integral circumferential upper surface of the at least one side wall, said at least one irregular shaped groove partially the same as the partial surface contours of the milk reservoir device;
   d. the circumferential upper surface of the milk storage device configured to receive and support the milk reservoir device with the pouring spout positioned below the circumferential upper surface of the milk storage device;
   e. the circumferential upper surface of the milk storage device configured to support the milk reservoir device along the partial surface contours of the milk reservoir device.

2. The liquid milk transfer system of claim 1, wherein:
   the milk storage device includes an upwardly extending neck communicating with the first opening; and
   the at least one irregularly shaped groove disposed in the neck.

3. The liquid milk transfer system of claim 2, wherein each of the at least one irregularly shaped groove has a first surface configured to engage a first surface of said milk reservoir device and a second surface configured to engage a second surface of said milk reservoir device.

4. The liquid milk transfer system of claim 3, wherein:
   the first surface of each at least one irregularly shaped groove is linear, and the second surface of each irregularly shaped groove is curved.

5. The liquid milk transfer system of claim 2, wherein:
   an outer surface of the neck includes external threads disposed below the circumferential upper surface;
   a removably attached nipple cap assembly having internal threads, the nipple cap assembly removably attached to the neck when the milk reservoir device is removed from the at least one irregularly shaped groove.

\* \* \* \* \*